US012092368B2

(12) United States Patent
Schnabelrauch

(10) Patent No.: US 12,092,368 B2
(45) Date of Patent: Sep. 17, 2024

(54) AIR TREATMENT APPARATUS HAVING A THERMOELECTRIC GENERATOR FOR CONTROLLING AIR FLOW AND SCENT DISPERSION

(71) Applicant: Justin Schnabelrauch, Ypsilanti, MI (US)

(72) Inventor: Justin Schnabelrauch, Ypsilanti, MI (US)

( * ) Notice: Subject to any disclaimer, the term of this patent is extended or adjusted under 35 U.S.C. 154(b) by 977 days.

(21) Appl. No.: 17/064,042

(22) Filed: Oct. 6, 2020

(65) Prior Publication Data

US 2021/0381721 A1  Dec. 9, 2021

Related U.S. Application Data

(60) Provisional application No. 63/034,858, filed on Jun. 4, 2020.

(51) Int. Cl.
*F24H 3/04* (2022.01)
*A61L 9/03* (2006.01)

(52) U.S. Cl.
CPC ............ *F24H 3/0494* (2013.01); *A61L 9/032* (2013.01); *A61L 9/037* (2013.01)

(58) Field of Classification Search
CPC ... A61L 9/00; A61L 9/015; A61L 9/02; A61L 9/03; A61L 9/032; A61L 9/037; F21V 35/00; F24H 3/00; F24H 3/02; F24H 3/04; F24H 3/0494
See application file for complete search history.

(56) References Cited

U.S. PATENT DOCUMENTS

| | | |
|---|---|---|
| 5,544,488 A | 8/1996 | Reid |
| 6,663,384 B2 | 12/2003 | Papai |
| 9,564,572 B2 | 2/2017 | Haider |
| 9,869,436 B2 | 1/2018 | Park |
| 11,092,300 B2 | 8/2021 | Schnabelrauch |
| 2004/0265760 A1 | 12/2004 | Swearingen |
| 2005/0277076 A1 | 12/2005 | Papai |
| 2018/0156403 A1 | 6/2018 | Millan |
| 2020/0332975 A1 | 10/2020 | Schnabelrauch |

FOREIGN PATENT DOCUMENTS

KR       10201435 B1 *  8/2019 ............... F21S 9/00

OTHER PUBLICATIONS

Machine translation of KR102014354B1, published on Aug. 26, 2019 (Year: 2019).*

* cited by examiner

*Primary Examiner* — Natasha E Young
(74) *Attorney, Agent, or Firm* — Mitchell Law PLLC; Matthew W. Mitchell

(57) ABSTRACT

A venting apparatus for a heat source is disclosed. The venting apparatus includes a venting housing structure comprising a plurality of exhaust apertures proximate to a heat collector, wherein the exhaust apertures vent into a chamber defined, in part, by a circumferential surface having a radial extent from the apertures, and a thermoelectric device in thermal communication to the heat collector on a second surface thereof.

19 Claims, 11 Drawing Sheets

AIR TREATMENT APPARATUS HAVING A THERMOELECTRIC GENERATOR FOR CONTROLLING AIR FLOW AND SCENT DISPERSION

CROSS REFERENCE TO RELATED APPLICATIONS

This application claims the benefit of Provisional Application No. 63/034,858 filed on Jun. 4, 2020 which is hereby incorporated herein by reference.

TECHNICAL FIELD

This disclosure relates to air flow devices, and more particularly to an air treatment apparatus having a thermoelectric generator for the controllable dispensing of fragrances, insect repellents, and/or other chemicals into the air.

BACKGROUND

The statements in this section merely provide background information related to the present disclosure and may not constitute prior art.

Candles in jars, i.e., containerized candles have been used for many years, primarily for lighting and decoration purposes. More recently, scented container candles in apothecary jars or similarly shaped vessels have become widely used. Many of these containerized candles are sold in standard sizes and shapes and used for dispersing a scent.

There are other known scent dispersers such as wax warmers or scent diffusers, but they require batteries or cords for powering the release of fragrance into the air. Insect repellent candles or electric scent diffusers are disadvantaged in outdoor settings. The candles can unevenly diffuse the scent into the air or be unduly affected by wind or breeze, which can cause uneven burning or flame extinguishment. Electronic diffusers such as personal repellent dispensers or insecticide diffusers, require batteries or power cords for powering the release of chemical repellents into the air, which can be limiting and inefficient.

Therefore, a need exists for an air treatment apparatus having a thermoelectric generator for means of portable scent diffusion.

SUMMARY

A venting apparatus for a heat source is disclosed. The venting apparatus includes a venting housing structure comprising a plurality of exhaust apertures proximate to a heat collector, wherein the exhaust apertures vent into a chamber defined, in part, by a circumferential surface having a radial extent from the apertures, and a thermoelectric device in thermal communication to the heat collector on a second surface thereof.

Certain embodiments of the chamber allow exhaust and scent from the candle to selectively and controllably mix with outside air directed from a fan.

Certain embodiments of the chamber mitigate undesirable outside airflow into a combustion chamber of a heat source.

This summary is provided merely to introduce certain concepts and not to identify key or essential features of the claimed subject matter.

BRIEF DESCRIPTION OF THE DRAWINGS

One or more embodiments will now be described, by way of example, with reference to the accompanying drawings, in which.

DETAILED DESCRIPTION

Figure 1:
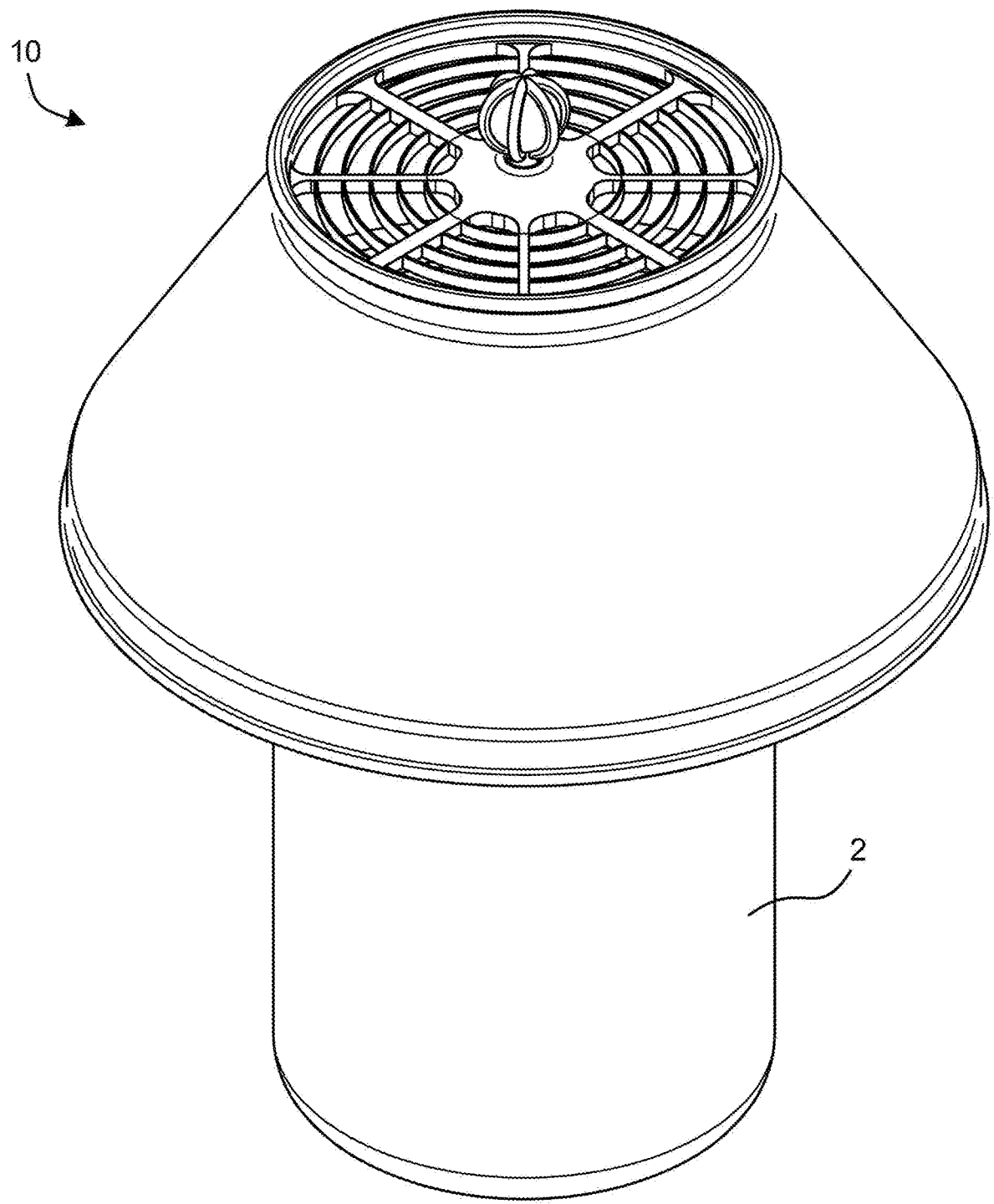
FIG. 1 shows an exemplary air treatment apparatus atop a scented container candle, in accordance with the present disclosure.
Figure 2:
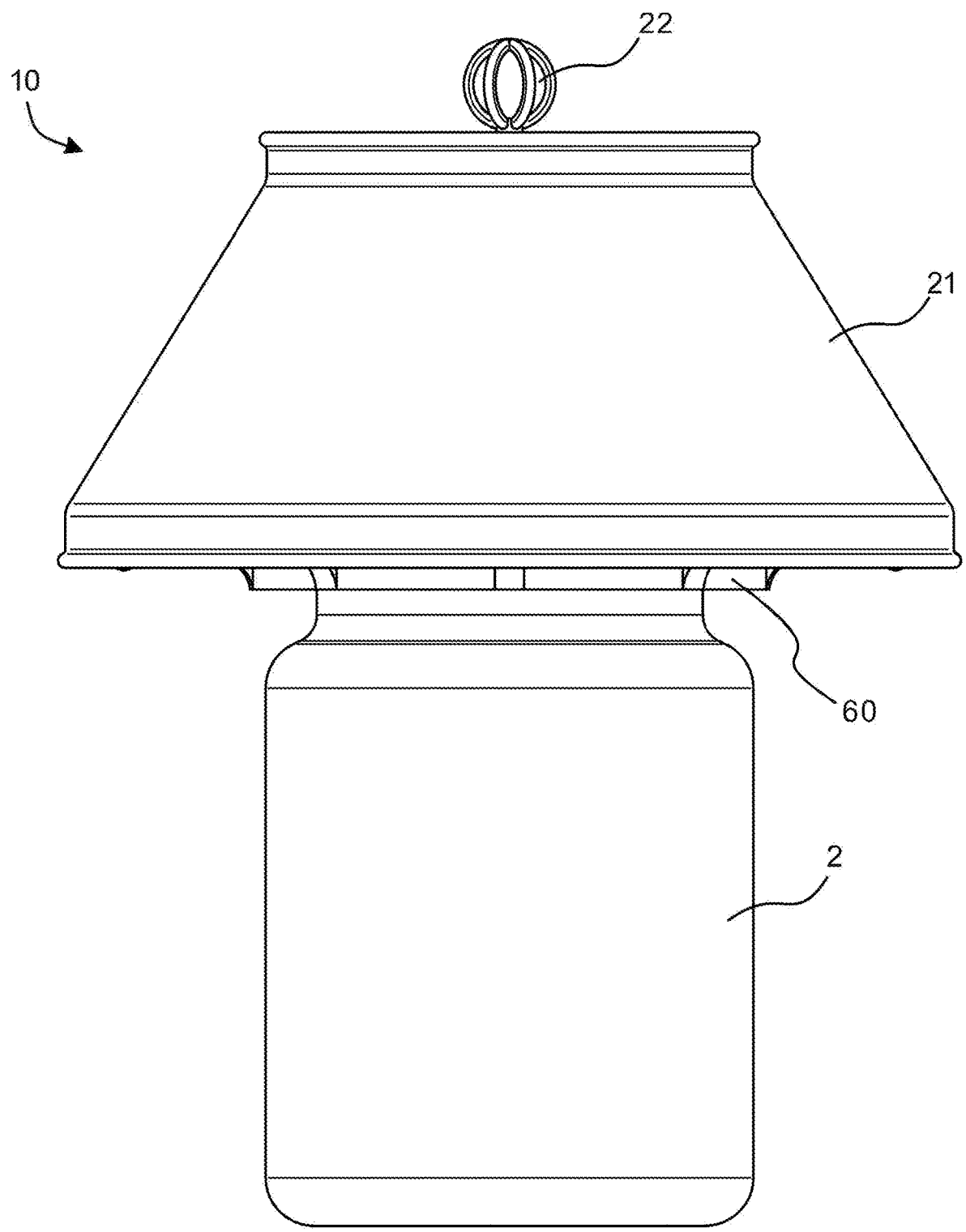
FIG. 2 is a side view of the air treatment apparatus atop a scented container candle, in accordance with the present disclosure.
Figure 3:
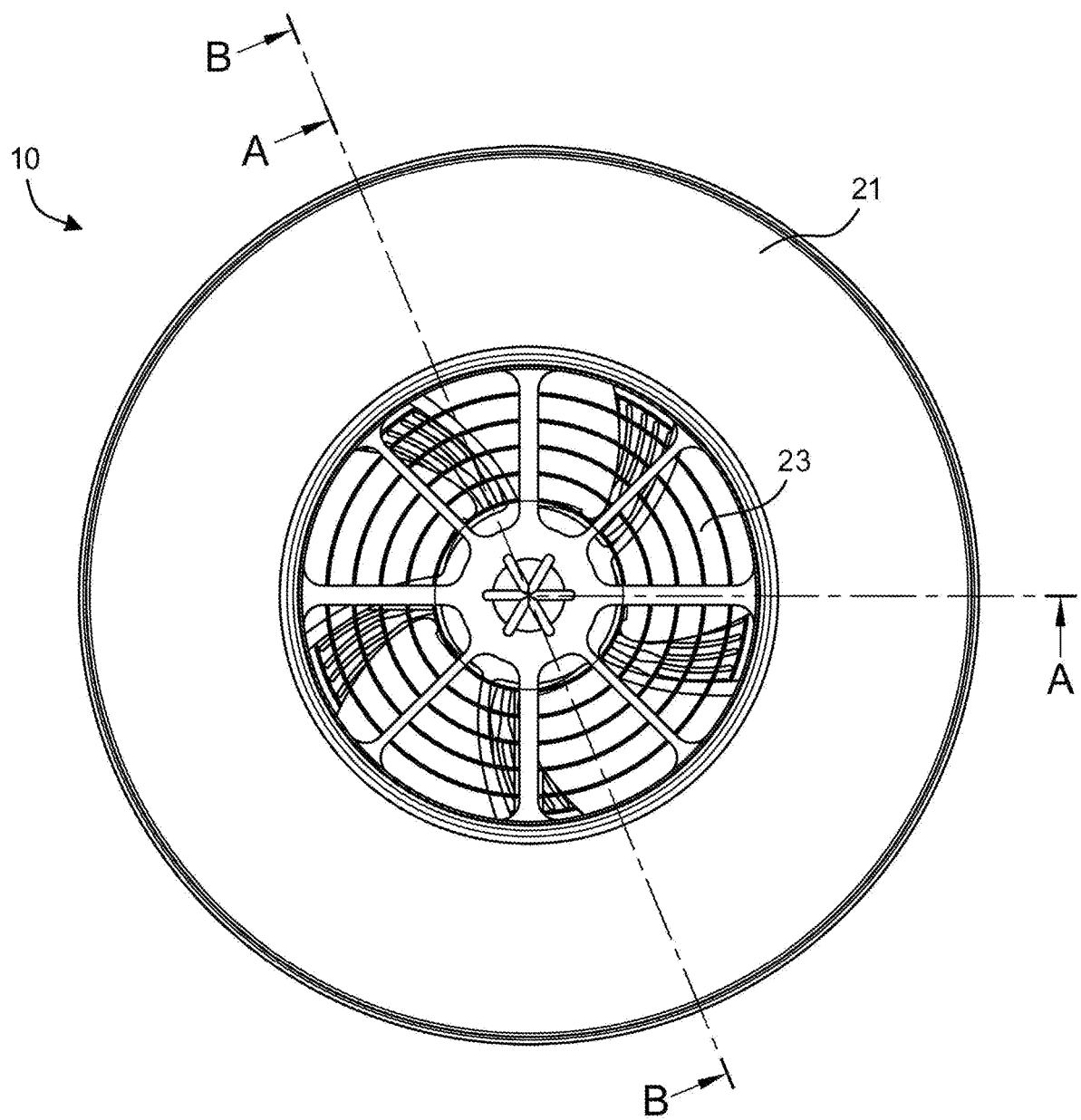
FIG. 3 is top view of the air treatment apparatus, in accordance with the present disclosure.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

As used in the description herein and throughout the claims, the following terms take the meanings explicitly associated herein, unless the context clearly dictates otherwise: the meaning of "a," "an," and "the" includes plural reference, the meaning of "in" includes "in" and "on." The term "based upon" is not exclusive and allows for being based on additional factors not described, unless the context clearly dictates otherwise. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner.

Referring to the drawings, wherein the depictions are for the purpose of illustrating certain examples only and not for the purpose of limiting the same, FIG. 1 shows an example of the air treatment apparatus 10 having a thermoelectric generator. The air treatment apparatus 10 is shown resting atop a containerized candle 2. The air treatment apparatus 10 is shown without a decorative design for ease of illustration. A decorative design may include, but is not limited to, an external 3-dimensional relief, painted artwork, printed artwork or stylized cutout feature in which the user can view the internal working motion of the device.

Figure 6:
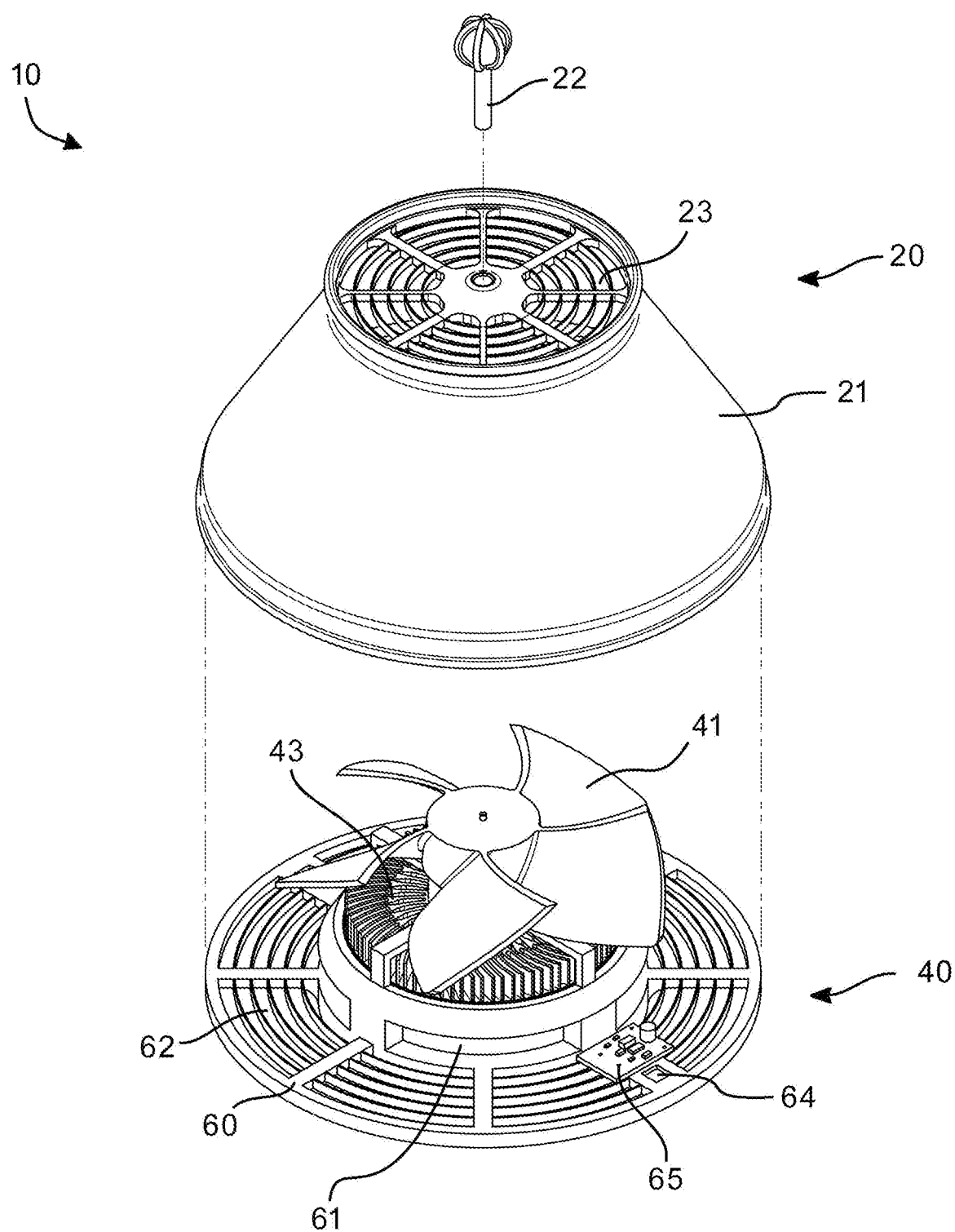
FIG. 6 is an exploded view of a housing module and a thermoelectric generator module, in accordance with the present disclosure.

The air treatment apparatus 10 includes a housing module 20 and a thermoelectric generator module 40, which is shown in FIG. 6. When assembled, the housing module 20 can be mechanically connected to the thermoelectric generator module 40, via a housing structure 21 and the venting structure 60. The housing structure 21 may engage the venting structure 60 via a press-fit, friction fit or other suitable attachment. In another example, the housing structure 21 uses protruding tabs for engagement to corresponding recesses on the venting structure 60 for secure coupling.

The housing module 20 includes mechanical elements to engage power indicator features of the apparatus 10, such as shown in FIG. 6. If desirable, a power indicator 22 can be easily positioned on or removed from the air treatment apparatus 10. In one example, the power indicator 22 is axially aligned with features of the housing structure 21 and engaged via the axle shaft of the electric motor 42 for selective rotation. A power indicator 22 may include a 3-dimensional ornament such as a sculpted finial. In the case of a sculpted ornament, the power indicator 22 provides both a visual and/or audible indication that the air treatment apparatus is in use and this indication is in addition to a lighting device 64. Other forms of indicators may include cutouts or a transparency in the housing structure 21 for the user to see the fan 41 in motion, indicating functional status of the air treatment apparatus.

The housing structure 21 may provide several functional purposes. One function is to provide air vent openings and structure for attachment of vent coverings, which in turn can be used to mount a thermoelectric generator module 40. Another purpose can be to direct the flow of air through the air treatment apparatus 10. The housing structure 21 can provide a barrier against wind or cross breeze and create a mixing chamber 25 within the structure of the device.

In one embodiment, the mixing chamber 25 is formed between an interior surface 90 of the housing structure 21 and surfaces 91 of the venting structure 60. The mixing chamber 25, is accessible via the apertures 61 and outlet air openings 62 and through the fan blades of a fan 41. Therefore, exhaust and scent from the candle 2 may be mixed with outside air from the fan 41 and/or outside air from the openings 62. In one embodiment, the openings 62 are formed by a series of vent fins, which may be formed in a series each having a circumferential shape and each being a different radial extent from the axle. In one embodiment, the mixing chamber 25, is substantially conically-shaped, less a radial extent from an axle or center, and less a top surface defined by the fan-blades. In one embodiment, the mixing chamber 25 is defined by, in part, a radial extent from the plurality of exhaust apertures $\alpha$.

In one embodiment, the housing structure 21 may include an attachment for an upper air opening and an attachment for lower air opening such as the venting structure 60. These air openings may include circular shapes or any shape consistent with the overall design (e.g. square or triangular). The exterior of the housing structure 21 may have decorative relief, painted, printed graphics or stylized cutout features.

Figure 7:
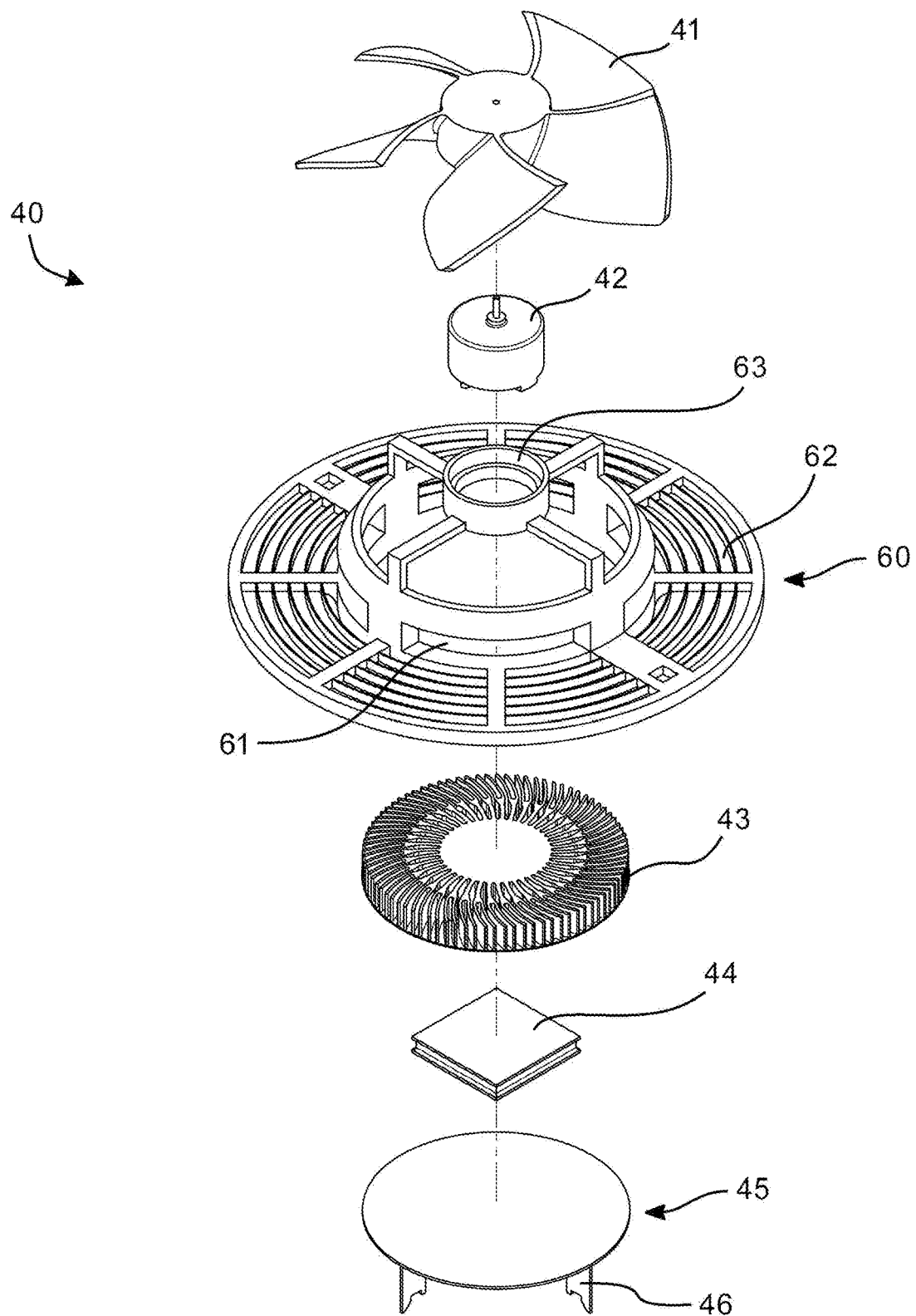
FIG. 7 is an exploded view of the thermoelectric generator module, in accordance with the present disclosure.

As shown in FIGS. 6 and 7, the thermoelectric generator module 40 includes a control device 65, which may be electrically connected to the thermoelectric generator module 44 and the electric motor 42. One or more lighting devices 64 such as light-emitting diode(s) may be used for operational or diagnostic informational communication.

The thermoelectric generator module 40 preferably includes a venting structure 60 that is sized and adapted for engagement to the housing structure 21, and sized for the attachment of the electric motor 42, heat sink 43 and heat collector 45. The housing structure 21 may be generally conically-shaped and can include a plurality of inlet air openings 23. The inlet air openings 23 are generally spaced circumferentially from the central axis of the housing module 20. The housing structure 21 is preferably a single contiguous, integral piece, but may be formed of any number of structures. In one example, the inlet air openings may be formed as part of a separate component that is assembled to the housing structure 21 as part of the housing module 20.

In one embodiment, the venting structure 60 is generally cylindrically-shaped and includes a plurality of exhaust apertures 61 and a plurality of outlet air openings 62. The outlet air openings 62 may be generally spaced circumferentially from the central axis of the venting structure 60. The exhaust apertures 61 may be generally radially aligned about the central axis of the structure 40. The exhaust apertures 61 are formed on the structure to be proximate to a heat collector 45 when the venting structure 60 is assembled as part of the thermoelectric generator module 40. The apertures or air vents are preferably spaced circumferentially or radially in any number so as to provide adequate air flow and for structural integrity purposes of the assembled apparatus 10.

The venting structure 60 is configured to accept the attachment of the electric motor 42 by use of a coupling feature 63. The venting structure 60 is preferably a single contiguous, integral piece, but may be formed of any number of structures. The structure is preferably formed of a non-combustible, low thermally conductive and deformable material such as a heat-resistant polymer or resin.

The thermoelectric generator module 40 is configured to generate electricity from a thermal potential generated from a heat source (e.g. a lit candle). It may communicate mechanical energy to one or more visual indicator elements 22, as desired. The module 40 can include a fan 41, an electric motor 42, a heat sink 43, a thermoelectric device (i.e., a TEG device) 44, a heat collector 45, and a coupling venting structure 60.

The fan 41 is axially connected, or integral with, an axle of the electric motor 42. The fan 41 includes a plurality of blades oriented to either direct air at or draw air away from the heat sink 43, depending on the direction of rotation.

The venting structure 60 includes a coupling feature 63 configured to receive the motor 42 and a cylindrical portion to receive the heat sink 43. Any number of radial spoke structures can provide support to the cylindrical central portion and an outer band that is sized and shaped for engagement to the housing structure 21.

The heat sink 43 is configured to contact the thermoelectric device 44. The thermoelectric device 44 generates electricity when there is a thermal difference between the heat sink 43 and the heat collector 45, the upper side and the bottom side, respectively. The heat sink 43 and the fan 42 are configured to extract, i.e., dissipate, thermal energy from the upper side of the thermoelectric device 44.

The heat collector 45 is configured to contact the thermoelectric device 44 and transmit thermal energy to a bottom side thereof. The heat collector 45 is further configured to engage or rest atop a lip of the candle 2. In one embodiment, the heat collector 45 includes a plurality of engagement stands 46 configured to straddle the lip of the candle 2 or engage a side thereof. The engagement stands 46 are radially aligned with a central axis of the thermoelectric generator module 40.

Components of the thermoelectric generator module 40 may be fastened together by screws, bolts or adhesive. It is important that there is quality contact of either the heat sink 43 to the upper side of the thermoelectric device 44 and by the heat collector 45 on the bottom side of the thermoelectric device 44. The tightness of the arrangement facilitates conductive heat transfer between the components for the desired thermoelectric power generation. In various embodiments, thermal conductivity may be enhanced through use of thermal paste or thermal pads placed between the thermoelectric device 44 and either or both of the heat sink 43 and heat collector 45. In some embodiments, tabs may be used for connections of the various components. The tabs can include a surface that is shaped to mate with one or more surfaces of another component to be positioned adjacent to the surface of the tab. Such surfaces can be used to provide support, force, and/or adjustment to one or more tabs being adjusted by the first and/or second component, among other benefits. The terms upper and bottom are used herein to aid the reader and are not to be viewed as limiting with respect to the present disclosure. Although shown as separate components for ease of illustration, some may be formed as an integral unit.

Figure 4:
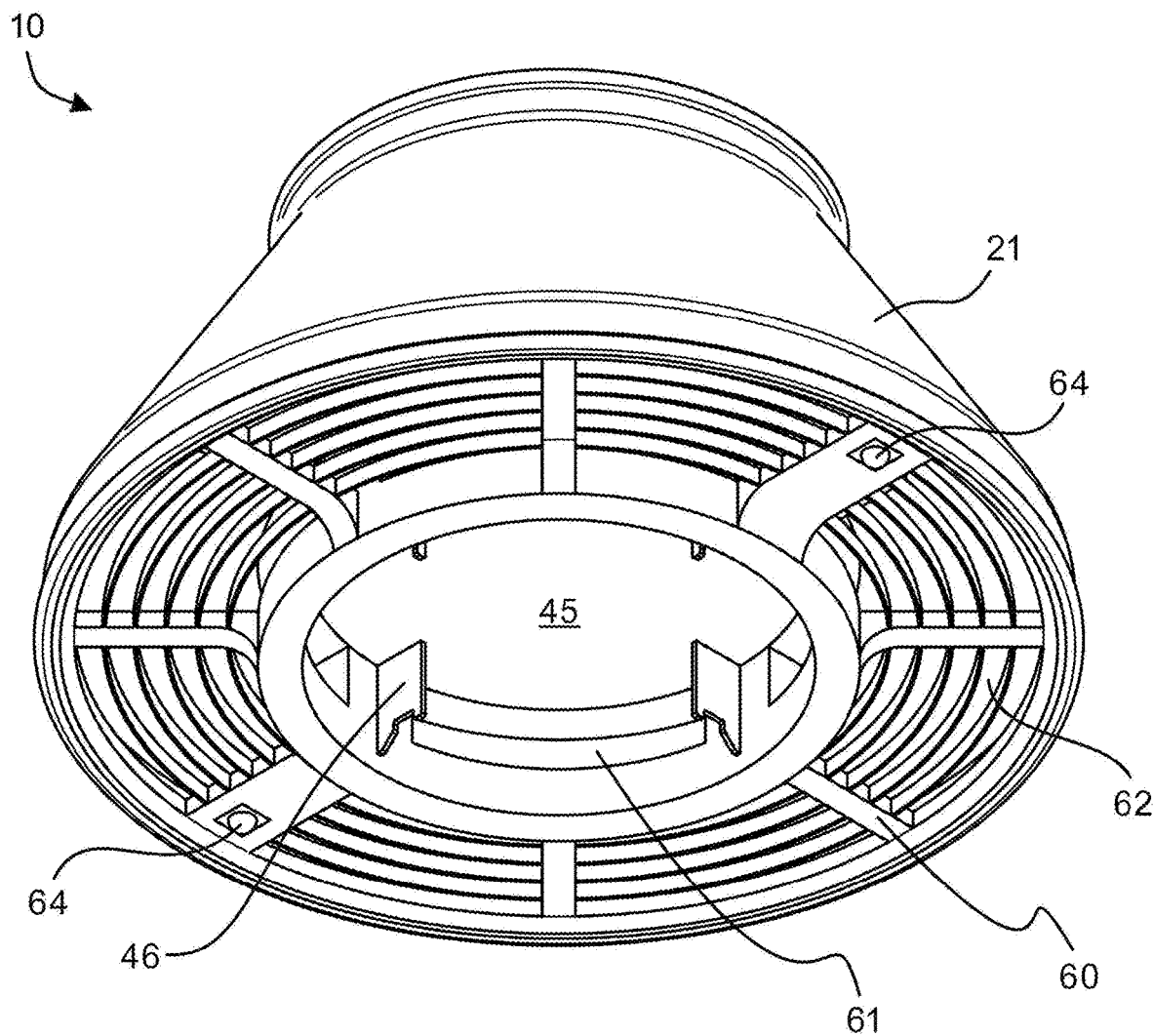
FIG. 4 is a lower isometric view of the air treatment apparatus, in accordance with the present disclosure.
Figure 8:
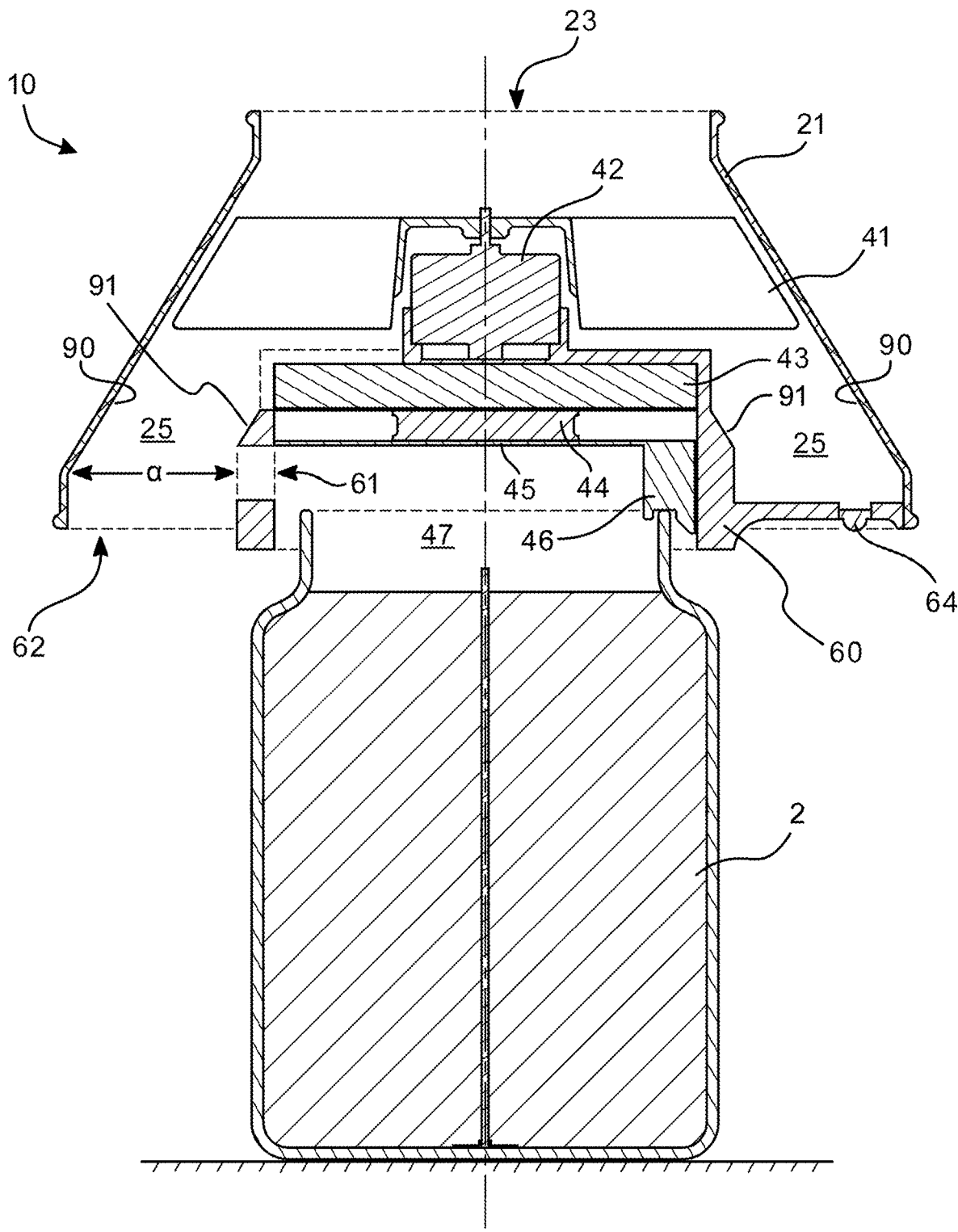
FIG. 8 is a cross-sectional view taken along line A-A of FIG. 3, in accordance with the present disclosure.
Figure 9:
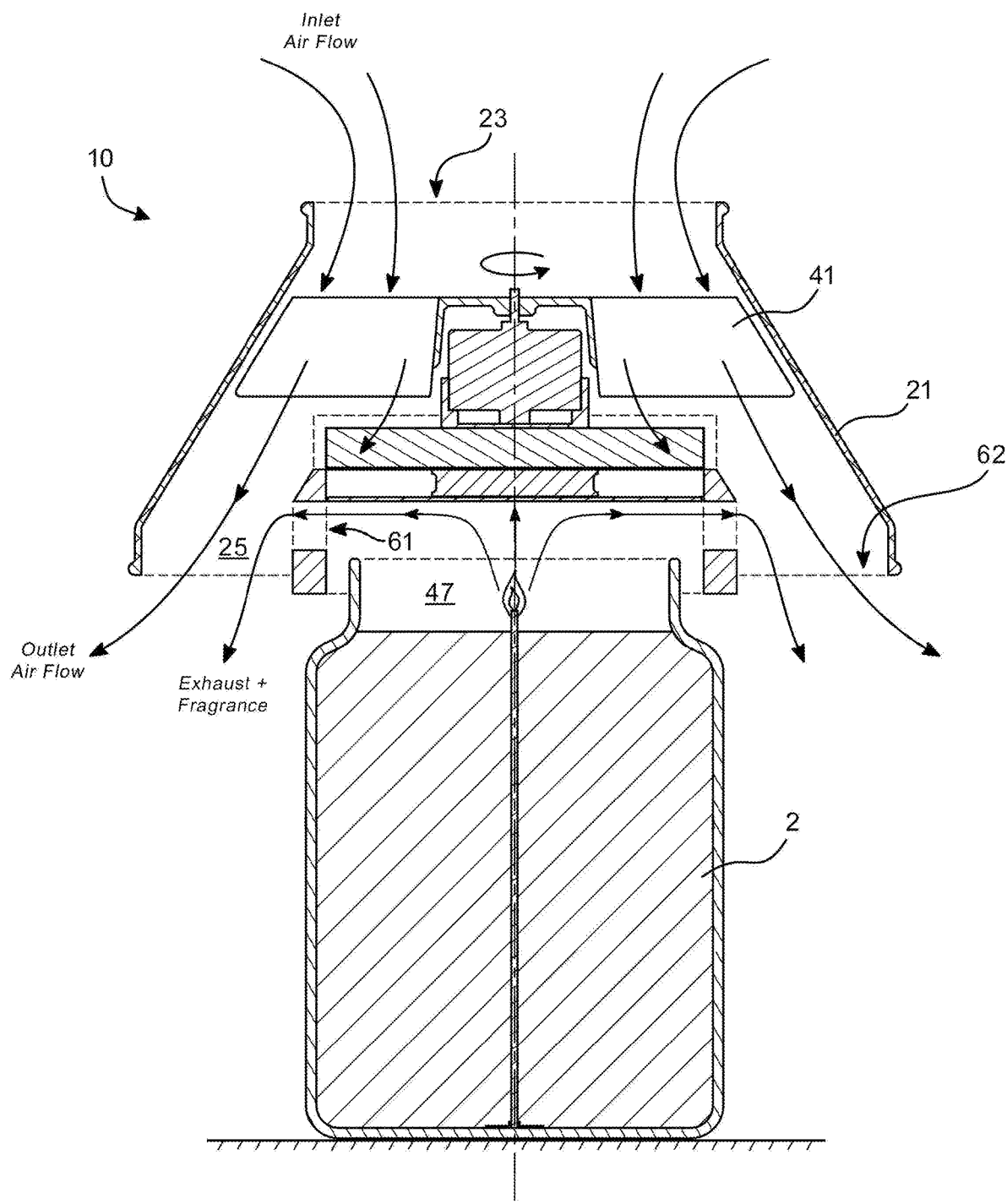
FIG. 9 is a cross-sectional view taken along line B-B of FIG. 3, showing air flow paths for the circulated air and the exhaust venting, in accordance with the present disclosure.
Figure 10:
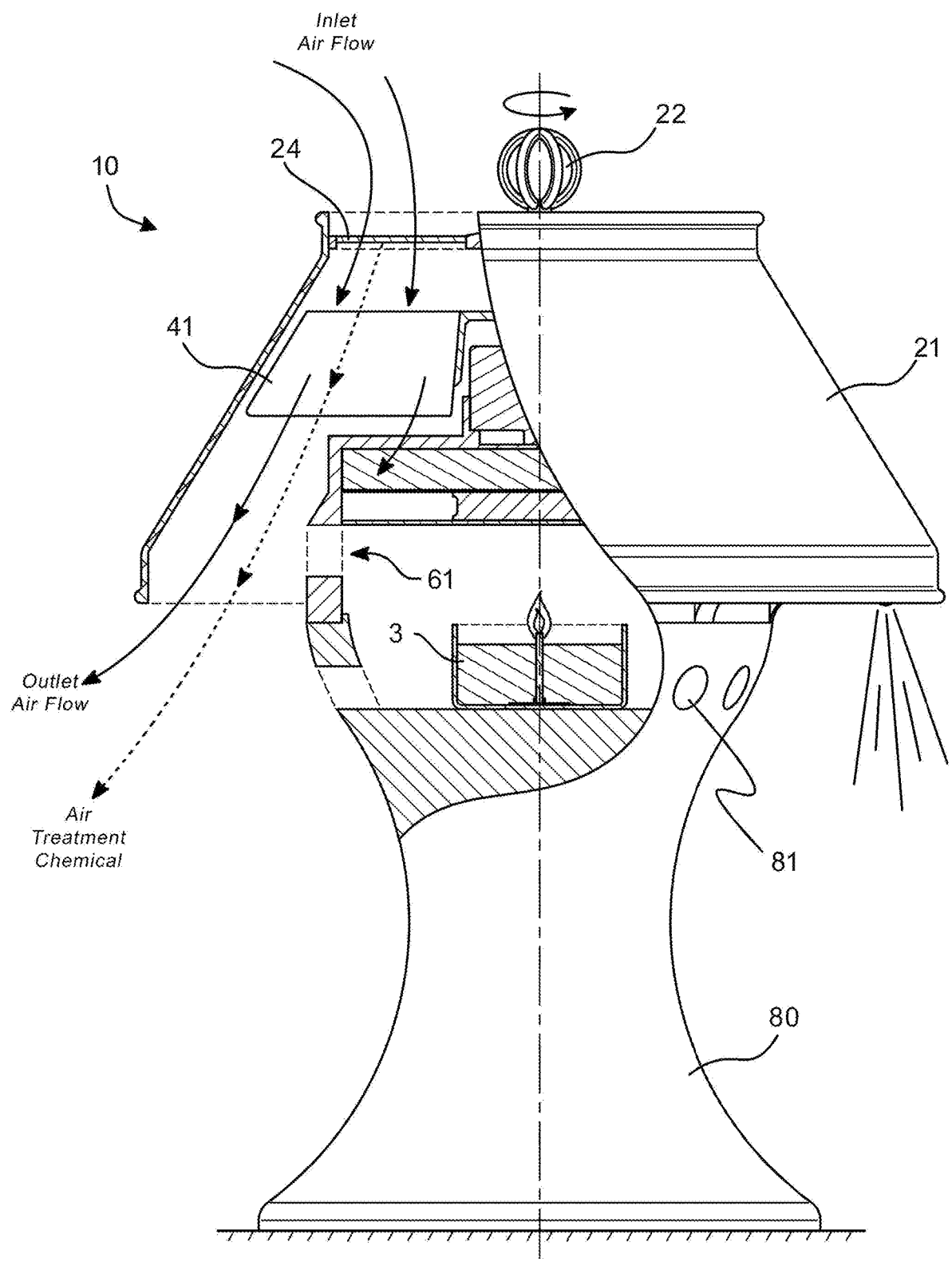
FIG. 10 is a partial cross-sectional view showing the air treatment apparatus in combination with a tea light candle in a candle holder structure and showing the air flow path when using an air treatment element, in accordance with the present disclosure.

With specific reference to FIGS. 4, 6, and 7, the exhaust apertures 61 are shown proximate to the heat collector 45. As shown in FIGS. 8, 9, and 10, the top of the exhaust aperture 61 is flush with a bottom surface of the heat collector 45. In this way, thermal energy from a heat source such as the lit candle 2 is immediately exhausted, reducing thermal build-up, and allowing preferential thermal dissipation by inhibiting flame heat to "pocket" or billow.

As FIG. 9 shows, thermal energy from the candle rises to the bottom surface of the heat collector 45, and then exhausts through the apertures 61. FIG. 8 shows the air treatment apparatus 10 in a cross-sectional view rotated on one side with respect to FIG. 9. As FIG. 8 shows, the engagement stands 46 are in the same horizontal plane as the apertures 61. The apertures 61 are formed between each of the engagement stands 46 to allow for preferential thermal exhaust.

With specific reference to FIG. 10, a further example of the air treatment apparatus 10 is shown which is intended to rest flush on a candle holder structure 80, configured to contain a small candle such as a tea light candle 3. In this example, the air treatment apparatus 10 includes air inlet apertures 81 and may include the engagement stands 46. The candle holder structure 80 is a cylindrically-shaped portion, with the capability of holding any number of candles, candle sizes and shapes. In one example, the candle holder structure 80 may be integrated with either the housing structure 21 or venting structure 60.

Figure 11A:
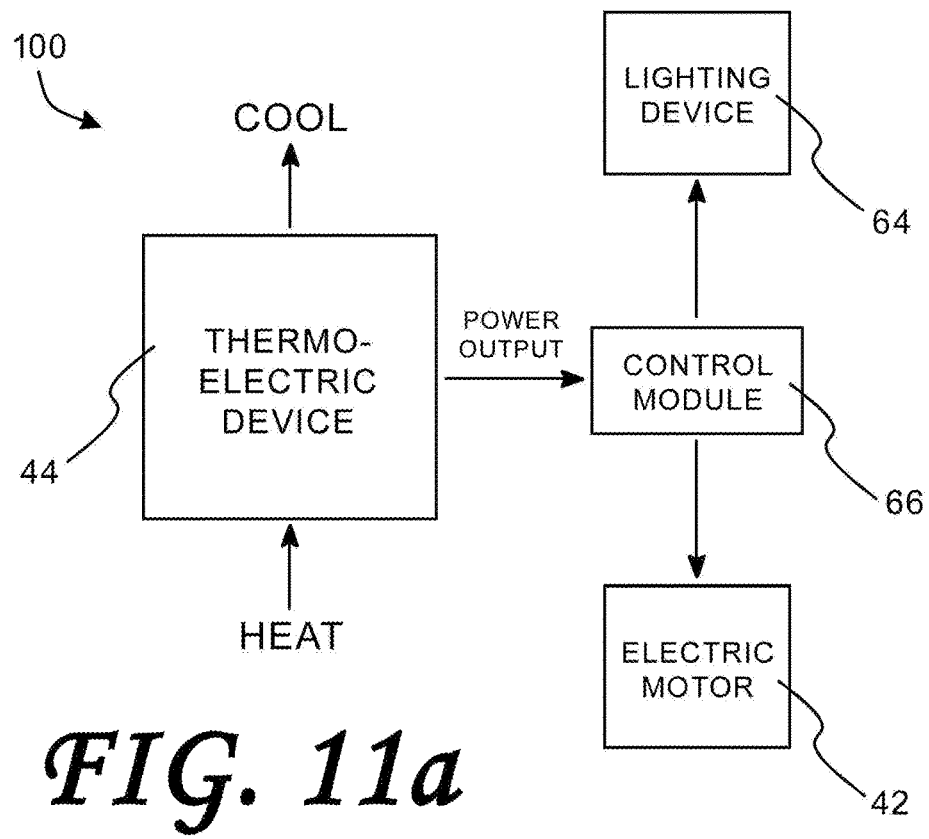
FIGS. 11A and 11B each schematically show an exemplary system for controlling the air treatment apparatus, in accordance with the present disclosure.
Figure 11B:
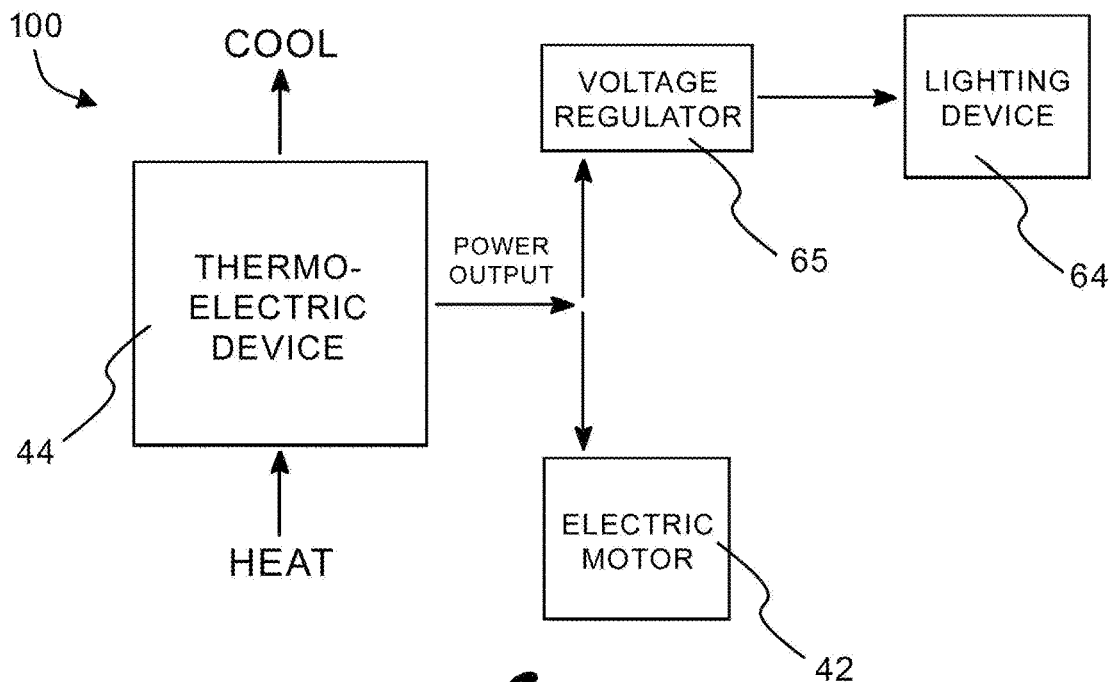

FIGS. 11A and 11B show embodiments of a system 100 that may be used to implement the electrical system of the air treatment apparatus 10. As FIGS. 11A and 11B show, the system 100 includes a thermoelectric device 44 and an electric motor 42. Various examples can include a voltage regulator 65 and/or a lighting device 64. In operation, heat is supplied from a heat source such as a containerized candle 2 or tea light candle 3. This thermal energy is converted to electrical energy by means of the thermoelectric device 44, which outputs electrical energy to the motor 42 and the voltage regulator 65 and lighting device 64.

In the example of the system 100 shown in FIG. 11A, a control module 66 receives the electrical energy from the thermoelectric device 44, which may then be selectively communicated to the motor 42 and the lighting device 64. In one example of the control module 66, it is configured to modulate electrical power from the thermoelectric device 44 before external communication thereof. In another example, the control module 66 is configured to control the speed and power of the motor 42. In one embodiment, the control module 66 includes one or more switches.

In the example of the system 100 shown in FIG. 11B, the voltage regulator 65 and the electric motor 42 receive electricity direct from the thermoelectric device 44, which may be selectively applied before or after the devices via one or more switches.

In use, the air treatment apparatus 10 is placed on a heat source, such as the candle 2 after the wick is lit. The heat collector 45 absorbs thermal energy rising from the flame of the lit candle 2. The thermal energy is transmitted to a bottom side of the thermoelectric device 44, creating a thermal difference between the top and bottom sides, which is converted to electrical energy therein taking advantage of the Seebeck effect. The electricity may be communicated to the control module 66 via electrical wires (not shown). The heat sink 43 dissipates heat to the environment through forced convection aided by the fan 41.

The fan 41 performs two primary functions; active heat dissipation and scent diffusion. The fan 41 provides forced convection air flow through the fins of the heat sink 43 to improve heat dissipation. The fan 41 also provides forced air flow through the housing structure 21 and past the exhaust aperture 61 to improve scent diffusion. Air flow and scent distribution rate increase with the rotational speed of the fan 41, resulting in a larger scent distribution range or area.

The fan 41 is propelled by an electric motor 42 which can be powered with electricity from the thermoelectric device 44 either directly, or through the control module 66. The electric motor 42 and fan 41 preferably have a common rotational axis and common central axis. The fan 41 provides consistent cooling for stable power generation that is not easily affected by fluctuating ambient air temperatures.

The fragrance and exhaust from the candle 2 is first released within the container or the structure of the candle 2; this area is the combustion chamber 47. The combustion chamber 47 is vented by means of the exhaust apertures 61, preferably positioned inset within the housing structure 21, thereby providing resistance to external wind or breeze. The fragrance and exhaust move from the combustion chamber 47 through the exhaust apertures 61 into the mixing chamber 25. The mixing chamber 25 is preferably positioned within the housing structure 21.

Once in the mixing chamber 25 the fragrance and exhaust is then mixed and accelerated by the air flow produced from the fan 41 before passing through the outlet air opening 62 for release into the surrounding environment.

Figure 5:
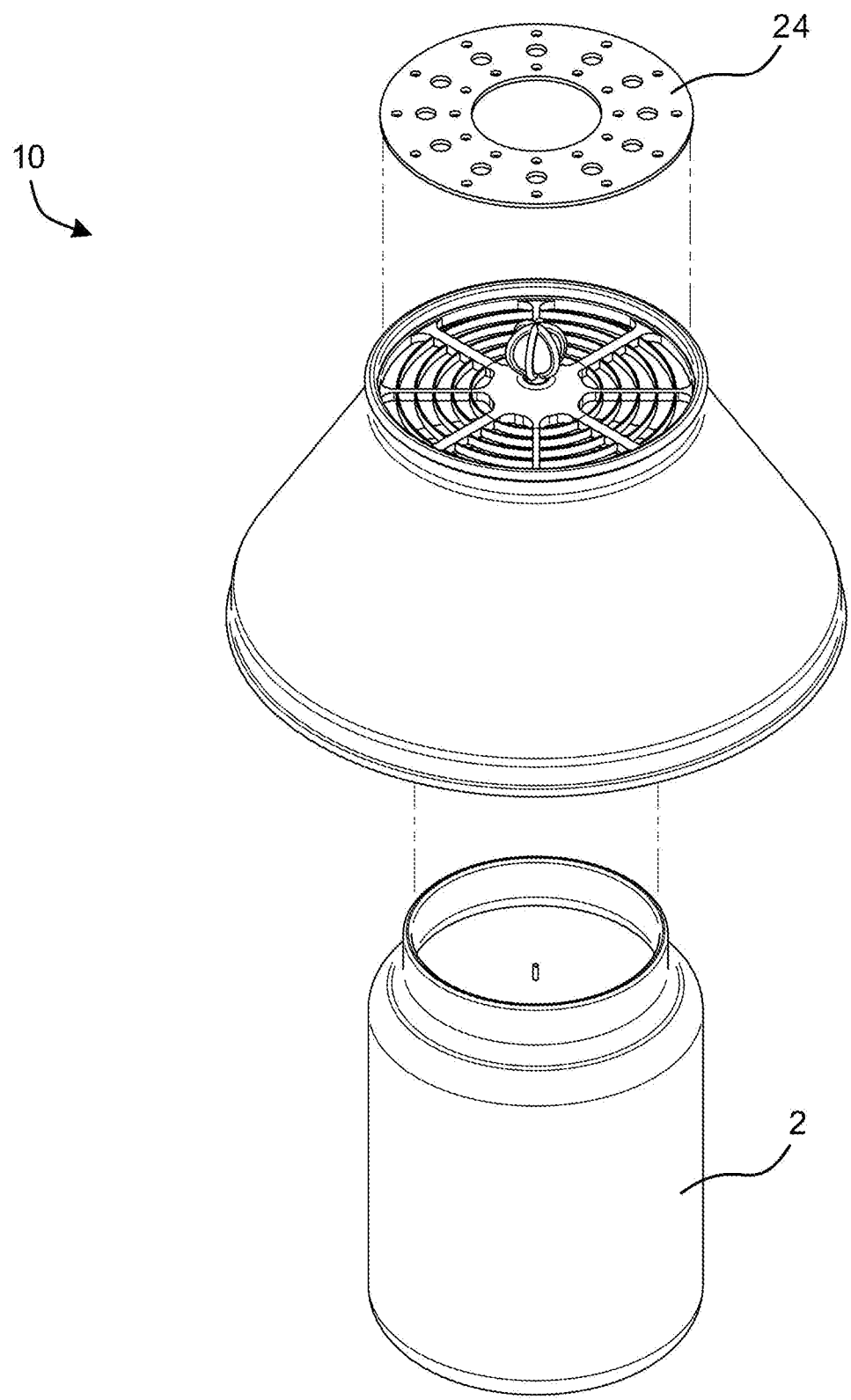
FIG. 5 is an exploded view of the air treatment apparatus showing its positioning on the container candle in combination with a disposable air treatment element, in accordance with the present disclosure.

In one example shown in FIGS. 5 and 10, an air treatment element 24 may be used as part of the air treatment apparatus 10. The air treatment element 24 may include but is not limited to a disposable woven material, fragrance infuser polymer or a module for dispensing essential oils.

It is preferable that the air treatment element 24 is easily removable to allow for quick transition between various elements containing different types of active ingredients or the use of successive elements holding the same active ingredient. In one example, a disposable air treatment element 24 may be positioning or attached to the inlet air opening 23. In another example, the air treatment element 24 may be positioning or attached to the outlet air opening 62. Alternatively, the structure of the inlet air opening 23 or outlet air opening 62 upper can be directly coated with the active ingredient for the air treatment.

Active ingredients used in the air treatment element 24 may be selected from a wide variety of formulations, and consist of various insect control materials, deodorizers, fragrances, sanitizers, and disinfectants known to be suitable for use with air dispersion. The chemical treatment can be pure active, or for ease of handling the material can be dissolved in a hydrocarbon or other solvent. One example of an air treatment formulation consists of a hydrocarbon solvent having a high boiling point (as a carrier), one or more active ingredients (e.g., a chemical repellent or insecticide), an antioxidant (for shelf life) and/or a fragrance. The formulation will be adapted for its specific application (e.g., indoor or outdoor use), and may have a variety of different ingredients and compounds.

The active ingredient may be applied to the air treatment element 24 by dripping, spraying, printing, or other conventional delivery of a liquid active ingredient and the ingredient amount can be selected so as to be depleted at the same time as the wax of a small tea light 3.

Alternatively, a container candle provides a large enough amount of wax to be sufficient for delivering the active ingredient from several successive air treatment elements 24. In that case, a usage gauge or cue (e.g., a color changing dye) can be added to the element to visually signal to the user that the air treatment ingredient has been depleted and that the element should be replaced.

While the foregoing disclosure discusses illustrative embodiments, it should be noted that various changes and modifications could be made herein without departing from the scope of the described embodiments as defined by the appended claims. Accordingly, the described embodiments are intended to embrace all such alterations, modifications and variations that fall within scope of the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiments, unless stated otherwise.

Benefits, other advantages, and solutions to problems have been described above with regard to specific embodiments of the present invention. However, the benefits, advantages, solutions to problems, and any element(s) that may cause or result in such benefits, advantages, or solutions to become more pronounced are not to be construed as a critical, required, or essential feature or element of any or all the claims. The invention is defined solely by the appended claims including any amendments made during the pendency of this application and all equivalents of those claims as issued.

The invention claimed is:

1. A venting apparatus for a heat source, the venting apparatus comprising:
    a venting housing structure comprising a plurality of exhaust apertures proximate to a heat collector, wherein the exhaust apertures vent into a chamber defined, in part, by a circumferential surface having a radial extent from the apertures, wherein the chamber is further defined by bottom openings into an exterior, and top openings through blades of a fan; and
    a thermoelectric device in thermal communication to the heat collector on a second surface thereof.

2. The venting apparatus of claim 1, wherein the chamber is substantially conically-shaped, less a radial extent from a center of the venting apparatus, and less a top surface defined by the blades of the fan.

3. The venting apparatus of claim 1, further comprising:
    a control device electrically connected to the thermoelectric device and connected to a motor of a fan, wherein the thermoelectric device is coupled to a heat sink on a side opposite the heat collector, and electrically coupled to the motor, wherein the motor is mechanically connected to the fan configured to thermally affect the heat sink and direct air into the chamber.

4. The venting apparatus of claim 3, wherein the motor is coupled to a support structure having a cylindrical, central portion having an opening that is configured to receive the motor, the cylindrical central portion being supported by a number of radially aligned spoke members, wherein the support structure is configured to engage an inner wall of the venting housing structure.

5. The venting apparatus of claim 1, wherein the exhaust apertures are spaced circumferentially with a central axis of the venting apparatus and are radially aligned with the central axis of the venting apparatus.

6. A venting apparatus for a heat source, the venting apparatus comprising:
    a venting housing structure comprising a plurality of exhaust apertures proximate to a heat collector, wherein the exhaust apertures vent into a chamber defined, in part, by a circumferential surface having a radial extent from the apertures, wherein the venting housing structure is configured to engage a lip of a containerized candle; and
    a thermoelectric device in thermal communication to the heat collector on a second surface thereof.

7. The venting apparatus of claim 1, wherein the plurality of exhaust apertures have an upper edge flush with a surface of the heat collector, wherein the heat collector has a flat, circular-shaped first surface.

8. A venting apparatus for a heat source, the venting apparatus comprising:
    a venting housing structure comprising a plurality of exhaust apertures proximate to a heat collector, having a flat, circular-shaped first surface, wherein the plurality of exhaust apertures are radially aligned with a central axis of the venting apparatus;
    a thermoelectric device in thermal communication to the heat collector on a second surface thereof and in thermal communication to a heat sink on an opposing side thereof, wherein the thermoelectric device is electrically coupled to a motor mechanically coupled to a fan; and
    an exterior surface hood forming an interior chamber for mixing exhaust from a heat source and air from the fan, wherein the chamber is accessible through the plurality of exhaust apertures.

9. The venting apparatus of claim 8, wherein the interior chamber is further defined by bottom openings into an exterior of the venting apparatus.

10. The venting apparatus of claim 9, wherein the interior chamber is substantially conically-shaped, less a radial extent from a center of the venting apparatus, and less a top surface defined by the blades of the fan.

11. The venting apparatus of claim 9, wherein the exterior surface hood is a radial extent from the plurality of exhaust apertures.

12. The venting apparatus of claim 11, wherein the exterior surface hood is substantially conically-shaped, less a radial extent from a center of the venting apparatus, and less a top surface defined by the blades of the fan.

13. The venting apparatus of claim 11, wherein the plurality of exhaust apertures have an upper edge flush with a surface of the heat collector, and wherein the exhaust apertures are spaced evenly, circumferentially with a central axis of the venting apparatus.

14. A venting apparatus for a heat source, the venting apparatus comprising:
- a venting housing structure configured to support a thermoelectric device, the venting housing structure comprising a plurality of exhaust apertures proximate to a heat collector, having a first surface, and a plurality of ambient air apertures proximate to a heat sink, wherein the plurality of exhaust apertures and the ambient air apertures are radially aligned with a central axis of the venting apparatus, wherein the plurality of exhaust apertures have an upper edge flush with a surface of the heat collector;
- wherein the venting housing comprises an exterior surface that forms an interior chamber defined by an interior surface of the exterior surface, the plurality of exhaust apertures, and a bottom, opening into an exterior of the venting apparatus; and
- a thermoelectric device in thermal communication to a heat collector on a second surface thereof and in thermal communication to an air shield and the heat sink on an opposing side thereof, wherein the thermoelectric device is electrically coupled to a motor, wherein the motor is mechanically connected to a fan configured to thermally affect the heat sink by directing air through the plurality of ambient air apertures, the fan further configured to direct outside air into the interior chamber.

15. The venting apparatus of claim 14, wherein the bottom opening is disc shaped, having a plurality of vent openings formed by vent fins.

16. The venting apparatus of claim 15, wherein the interior chamber is further defined by the blades of the fan.

17. The venting apparatus of claim 16, wherein the interior surface of the exterior surface is a radial extent from the plurality of exhaust apertures, and wherein the interior chamber is substantially conically-shaped, less a radial extent from a center of the venting apparatus, and less a top surface defined by the blades of the fan.

18. The venting apparatus of claim 17, further comprising:
- a disc having a plurality of inlet air openings, the disc being an air treatment element.

19. The venting apparatus of claim 18, wherein the plurality of exhaust apertures have an upper edge flush with a surface of the heat collector, and wherein the exhaust apertures are spaced evenly, circumferentially with a central axis of the venting apparatus, wherein the motor is coupled to a support structure having a cylindrical, central portion having an opening that is configured to receive the motor, the cylindrical central portion being supported by a number of radially aligned spoke members, wherein the support structure is configured to engage an inner wall of the venting housing structure, wherein the venting housing structure further comprises a plurality of engagement stands configured to straddle and engage a lip of a containerized candle, wherein the engagement stands are radially aligned with the central axis of the venting apparatus and spaced evenly around a circumference thereof.

* * * * *